United States Patent
Kojima et al.

[11] Patent Number: 5,971,962
[45] Date of Patent: Oct. 26, 1999

[54] SKIN BUTTON

[75] Inventors: Akira Kojima, Kiryu; Kenji Yamazaki, Koganei; Toshio Mori, Chino; Sakashi Kobayashi, Nagano-ken; Osamu Tagusari, Tokyo, all of Japan

[73] Assignee: Sun Medical Technology Research, Japan

[21] Appl. No.: 09/037,928

[22] Filed: Mar. 10, 1998

[30] Foreign Application Priority Data

Mar. 11, 1997 [JP] Japan .................................... 9-097873
Dec. 8, 1997 [JP] Japan .................................... 9-368584

[51] Int. Cl.⁶ .................................................. A61M 25/02
[52] U.S. Cl. .......................................... 604/175; 604/174
[58] Field of Search ............................ 606/108; 604/174, 604/175; 128/DIG. 26

[56] References Cited

U.S. PATENT DOCUMENTS

| | | | |
|---|---|---|---|
| 1,080,934 | 12/1913 | Shackleford | 604/174 |
| 3,663,965 | 5/1972 | Lee, Jr. et al. | |
| 4,217,664 | 8/1980 | Faso | 604/175 |
| 4,318,401 | 3/1982 | Zimmerman | 604/174 |
| 4,344,435 | 8/1982 | Aubin | 604/285 |
| 4,393,873 | 7/1983 | Nawash et al. | 604/174 |
| 4,417,888 | 11/1983 | Cosentino et al. | 604/175 |
| 4,488,877 | 12/1984 | Klein et al. | 604/175 |
| 4,534,761 | 8/1985 | Raible | 604/175 |
| 4,596,560 | 6/1986 | Simpson | 604/174 |
| 4,634,422 | 1/1987 | Kantrowitz et al. | |
| 5,048,512 | 9/1991 | Turner et al. | 128/DIG. 26 |
| 5,122,122 | 6/1992 | Allgood | 604/174 |
| 5,242,391 | 9/1993 | Place et al. | 604/285 |
| 5,251,616 | 10/1993 | Desch | 128/DIG. 26 |
| 5,501,216 | 3/1996 | Byrd | 604/174 |
| 5,599,311 | 2/1997 | Raulerson | 604/174 |
| 5,640,977 | 6/1997 | Leahy et al. | 604/174 |
| 5,776,110 | 7/1998 | Guy | 604/174 |
| 5,803,922 | 9/1998 | Christy | 606/108 |
| 5,807,341 | 9/1998 | Heim | 604/174 |

FOREIGN PATENT DOCUMENTS

| | | |
|---|---|---|
| 0 343 114 | 11/1989 | European Pat. Off. |
| 0 367 354 | 5/1990 | European Pat. Off. |
| 0 383 568 | 8/1990 | European Pat. Off. |
| 58-092360 | 6/1983 | Japan |
| 61-122870 | 6/1986 | Japan |
| 6-233811 | 8/1994 | Japan |
| WO 97/02848 | 1/1997 | WIPO |

*Primary Examiner*—Paul J. Hirsch
*Attorney, Agent, or Firm*—Nixon & Vanderhye

[57] ABSTRACT

A skin button comprising a cylindrical core component secured in the subcutaneous tissue of the living body as passing through the tissue, the core component has thorough holes which pass through the subcutaneous tissue and let skin penetrating components be inserted which pass into and out of the subcutaneous tissue, the core component has a tubular component made of fiber base material consisting of biocompatible fibers on the rim of the part of the core component which contacts the living tissue. The living tissue grows into the space among fibers of basic fiber materials of the tubular component to securely hold this skin button in the subcutaneous tissue as well as to ensure prevention of bacterial infection.

6 Claims, 7 Drawing Sheets

SKIN BUTTON

BACKGROUND OF THE INVENTION

The present invention relates an apparatus to fix tubes, electric wires, and the like which pass through the skin of the living body, to the skin of the living body, that is, a skin button. More particularly, the present invention relates to an apparatus which is established at the site where tubes or electric wires pass through the skin of the living body which connect an organ in the living body or an artificial organ such as an artificial heart or an artificial heart-lung with an equipment and the like outside the body, and which sustains tubes, electric wires, and the like to the skin of the living body, the tubes and electric wires are fixed to the skin of the living body as they pass through the skin.

Conventionally, a procedure has been performed, where a tube is inserted into the living body by passing through the skin of the living body to inject pharmaceutical solution to an organ in the living body or to drain body fluid and the like from the living body. A procedure has also been performed where an electric wire is inserted into the living body by passing through the skin of the living body to pickup a signal from various detectors implanted in the living body. Moreover, tubes and electric wires have been inserted into the living body which connect an artificial organ implanted in the body such as an artificial heart or an artificial heart-lung with an equipment outside the body and supply pharmaceutical solution on electric power to the artificial organ. Various apparatus other than the above may be left in place as they pass through the skin of the living body for various purposes.

When the above tubes or electric wires, or any other apparatus are left in place as they pass through the skin of the living body for a long time, it is necessary to fix and sustain them to the skin as well as to give such a treatment to prevent invasion of bacteria into the body from this penetrating site.

Conventionally, a tabular component has been stuck to the surface of the skin around the penetrating site where a tube or an electric wire pass through the skin which, for example, connects an artificial heart implanted in the body and an equipment outside the body in order to make the above tube or electric wire pass through that component. In such a component, a load applied to the tube or the electric wire is transmitted dispersedly to the surrounding skin via that tabular component, whereby the tube or the like is fixed to the skin.

However, such a tabular component is stuck to the skin, so that when the skin moves because of body activity in use of the above component, the tabular component cannot coordinate with that movement of the skin, which may make the user feel discomfort or a pain. The above tabular component, which is stuck to the surface of the skin, is possible to move due to the elasticity of the skin. Therefore, when an external force is applied to this tube and the like, this tabular component moves, and as a consequence, the external force applied to the tube may be exerted on the through hole, causing a pain. Moreover, such a component allows possible invasion of bacteria from the site between the tube and the through hole of the skin.

Coating with a biocompatible material of the surface of a component like the above one which is left in the living body for a long time has been practiced conventionally. Such a measure allows sticking of the living tissue to the component, sustaining of the component to the living tissue, and prevention of viral invasion from the site where the component is buried. Such biocompatible materials include carbon materials, titanium, fluororesin, hydroxyapatite and the like, which are used as dental and bone prostheses.

However, the component of the present invention which is left in the living tissue as it passes through the skin, that is, a skin button, did not show sufficient bonding to the living tissue when the above conventional biocompatible materials were used.

In the past, a component to be left in the living body itself has been made of the above material, or alternatively, a component made of another material has had its surface coated with the above biocompatible material. Thus there has not been sufficient bonding of the surface of that component to the living tissue, which might cause a slippage between the surface of that component and the living tissue.

Therefore, the above tube which has its surface coated with a biocompatible material as was the case in the past will cause the movement of this tube due to distortion of the skin, cause some slippage between the penetrating site and the living body, and make the user feel a pain, and may allow the invasion of virus from the site.

BRIEF SUMMARY OF THE INVENTION

The present invention, based on the above background, provides an apparatus which securely fits and sustains tubes, electric wires, and the like which pass through the skin of the living body as mentioned above, causes no discomfort, and allows prevention of bacterial infection and the like, that is, a skin button.

A skin button of the present invention has a core component to attain the above object. The core component has a length at least sufficient to pass through the subcutaneous tissue of the living body to which this apparatus is applied. The core component also has at least one through hole, where a skin penetrating component such as a tube or an electric wire to pass through the skin is inserted, and the penetrating component passes through the core component. The space between the outer surface of the skin penetrating component and the inner surface of the through hole is provided with liquid-tight seal.

The outer surface of the core component, at least the part which contacts the living tissue, is covered with a tubular component made of a biocompatible material. This tubular component is made of a material which has a compatibility with the living organism. In the present invention, the material composing this tubular component consists of a fiber base material made of biocompatible fiber. The fiber material composing the tubular component consists of materials which are chemically inactive and well compatible with the living body including carbon fiber, titanium fiber, fluororesin fiber, hydroxyapatite fiber and the like. This tubular component may be composed of fiber base material made of such fiber materials in the form of woven, knitted or nonwoven fabric, or in the form of sponge or felt.

Since the above mentioned material is favorably compatible with the living body, the subcutaneous tissue where the skin button is buried grows and adheres closely to the surface of the tubular component to maintain the skin button in the predetermined place and to prevent bacterial infection. Moreover, the tubular component is composed of the fabric of the above mentioned fibers, and the grown subcutaneous tissue adheres closely to the component by getting into the space among fibers to integrate this skin button into the skin more securely, which prevents the user from feeling a pain due to the slippage between the skin button and the subcutaneous tissue and also ensures the prevention of bacterial infection between the skin button and the subcutaneous tissue.

In one preferred embodiment of the present invention, a collar-like flange portion projecting from the rim of the core component of the skin button, is provided. This flange, for example, may be so buried in the subcutaneous tissue that it lies between the straight muscle of abdomen and the rectus sheath of in the subcutaneous tissue of the body, which further ensures the bonding of the skin button to the subcutaneous tissue.

In an alternative preferred embodiment of the present invention, the surface of the part contacting the subcutaneous such as the above tubular component, flange portion, and the like is coated with, for example, law temperature pyrolytic carbon (LTPC) processed by chemical vapor deposition (CVD). Such carbon coating improves the compatibility of the surface with the living tissue to ensure the integration of the skin button with the subcutaneous tissue. Moreover, such carbon coating allows adhesion between the above tubular and core components, which avoids the necessity of use of another adhesive agent for their junction and improves the compatibility of the skin button with the living body.

Further oxygen plasma processing by contacting oxygen plasma with the surface of the above carbon coating layer further improves the compatibility of the carbon coating with the living body.

In another preferred embodiment of the present invention, the skin button of the present invention comprises a sleeve component where skin penetrating components such as tubes or electric wires pass through, and the above core component is placed around the perimeter of the cylindrical component. Between the core and sleeve components lie a spacer and an elastic membrane, or a hollow, doughnut-shaped elastic component and the like, which allows a structure ensuring that the core component can freely slide to the axial direction of the sleeve component as well as ensuring a seal between them. Therefore, when a load is applied to a skin penetrating component such as a tube, the sleeve component where the tube passes through and the core component buried in the subcutaneous tissue show relative axial movement to allow a certain movement of the tube, reducing the load transmitted from the core component to the subcutaneous tissue and the discomfort or pain the user may feel.

In another preferred embodiment of the present invention, a holder component which contacts the outer surface of the subcutaneous, that is, the epidermis, is provided. The holder component is so attached that it can rotate at the distal edge of the core component and it maintains the seal, and skin penetrating components such as tubes and electric wires pass through these core and holder components. Therefore, when a load is applied to such a tube, this load is dispersedly transmitted to the surface of the skin via the above holder component, and the load due to torsion of the tube and the like is absorbed by the rotating movement of the holder and core components, reducing the load transmitted from the core component to the subcutaneous tissue and the discomfort or pain the user may feel.

In another preferred embodiment of the present invention, there is an extension holder component placed on the distal edge of the core component, is provided. This extension holder component sustains part of tubes and the like directed to the outside of the body, while one or more points of this component closely contact the surface of the skin, serving as a guide for such tubes and the like directed to the outside as well as transmitting the load applied to these tubes and the like from the contact point to the surface of the skin, which reduces the load applied to the core component as well as reduces the discomfort or pain the user may feel.

In another preferred embodiment of the present invention, the tubes and the like directed to the outside of the body are sustained with a belt, which is worn around the surface of the living body and sustains the tubes and the like directed to the outside, ensuring the sustainment of the tubes and the like directed to the outside of the body, further reducing the load applied to the core component, and reducing the discomfort or pain the user may feel.

In another preferred embodiment of the present invention, the tubular component placed around the perimeter of the above core component is formed in a tapered from where the diameter reduces as the tubular component advances distally from the body. The subcutaneous tissue contacting the surface of this tubular component grows and adhere to the surface of the tubular component, and during the process, abnormal growth of the subcutaneous tissue, that is, down growth, may occur due to the contact pressure and the like imposed to the subcutaneous tissue by the tubular component. However, the tapered form of the tubular component allows axial movement of the tubular component in accordance with the growth of the subcutaneous tissue contacting the surface of the tubular component, leading to the prevention of the above mentioned down growth.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1A:
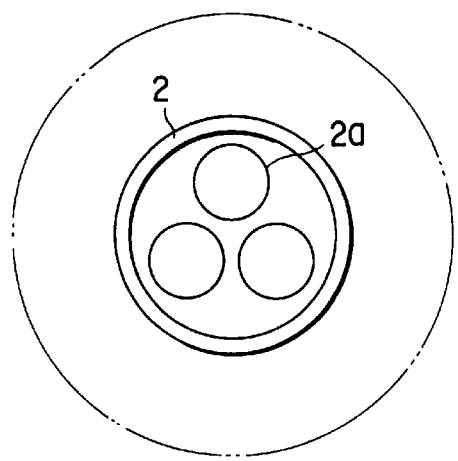
FIGS. 1A and 1B are front and longitudinal section views of the skin button in the embodiment 1 of the present invention, respectively.
Figure 1B:
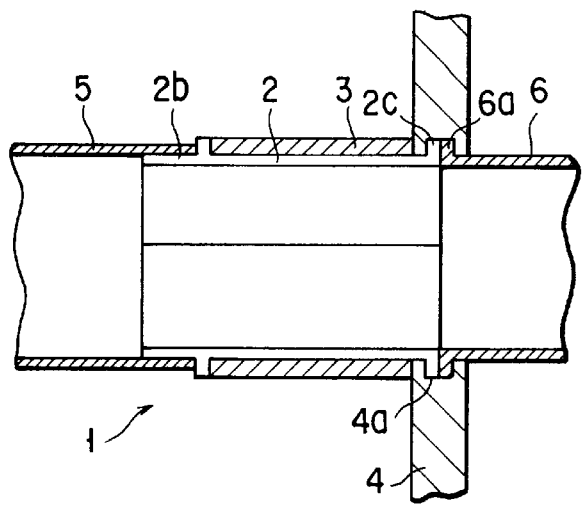
Figure 3:
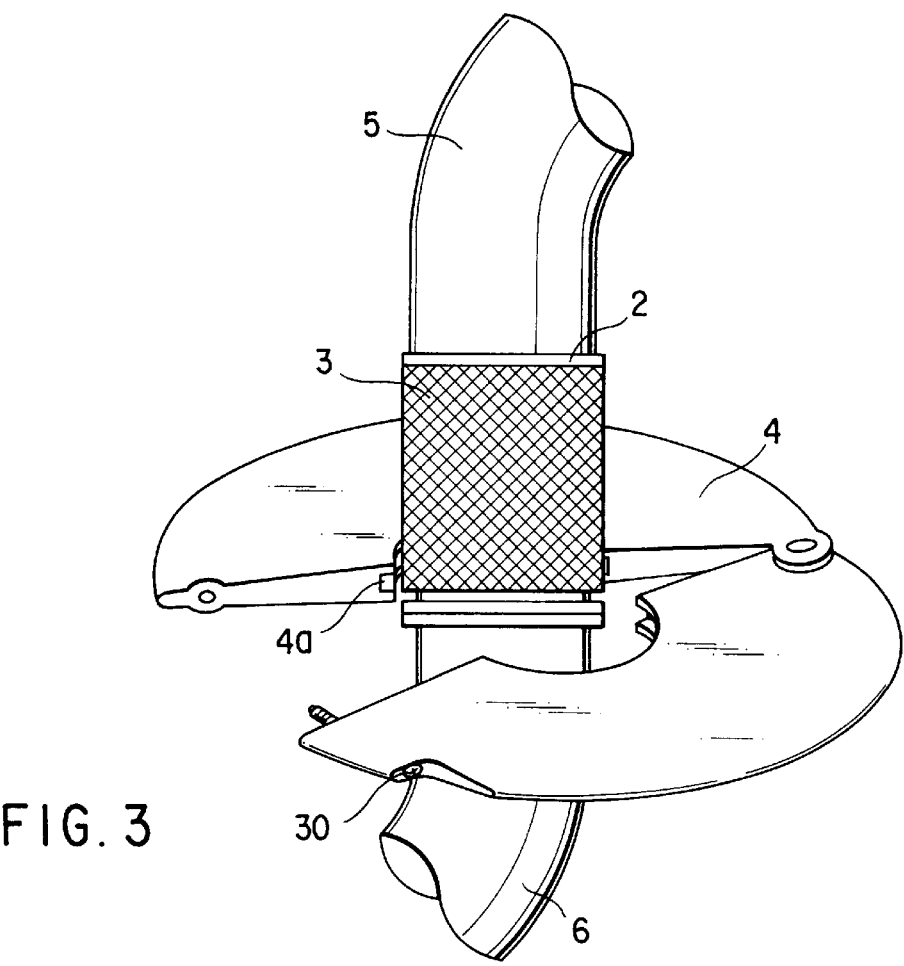
FIG. 3 is a exploded perspective view illustrating the attachment of the core and flange components of the skin button of FIG. 1.

The present invention will be described in detail below with reference to the drawings. FIGS. 1A, 1B and 3 illustrate the skin button in the embodiment 1, which is buried, for example, in the subcutaneous tissue of the living body, and lets skin penetrating components such as tubes and electric wires connecting an artificial organ implanted in the living body with an equipment outside the body entering into the body via the skin. FIGS. 1A and 1B are front and longitudinal section views, respectively.

In these figures, the numeral 1 is the skin button in the prevent invention, and the skin button 1 comprises a hollow, cylindrical core component 2, and a tubular component 3 made of a tubular biocompatible material placed around the perimeter of the core component 2. A flange component 4 is attached to the proximal edge of the core component 2. In this embodiment, the above tubes or electric wires are housed in coated tubes. A coated tube on the side of an equipment outside the body and a coated tube on the side of an artificial organ inside the body are designated by the numeral 5 and 6, respectively, both of which house the above tubes or electric wires inside.

The above core component 2 is made of titanium or carbon material which ensure air-tightness and prevention of bacterial infection with a fine rahmen surface (FRS) layer made of carbon fibers as a surface finish.

The core component 2 has three through holes 2a in order to let pass and hold electric cables connecting an artificial organ in the living body with an outside equipment (not shown) in the figure which drives the artificial organ, cooling water, drug solution, body fluid and the like (hereinafter, referred to as cables and the like). The number of these through holes 2a can be varied depending on the number of connected cables and the like.

A coated tube 5 on the side of outside equipment housing cables and the like is secured on the connecting portion 2b at one edge of the core component 2, while a collar portion 6a formed on the coated tube 6 on the side of the artificial organ is attached on the connecting collar portion 2c at the other edge.

Around the perimeter of the core component 2, a tubular component 3 made of carbon fiber base material treated with low temperature pyrolytic carbon (LTPC) by chemical vapor deposition (CVD) processing is hooked and attached, and securely adhered to the core component by such measures as press fitting, adhesion, CVD etc.

Since carbon fiber base material treated with low temperature pyrolytic carbon is strongly adhered to the core component by the bonding power of the middle layer through chemical vapor deposition processing, it can gain better biocompatibility than using of adhesive materials. Base materials for the tubular component include titanium nonwoven fabric, fluororesin nonwoven fabric, hydroxyapatite and the like which are inactive and favorably biocompatible, which may be in the form of knitted or nonwoven fabric or sheet of carbon fiber, sponge, or felt, or even in the shape of bobbin winding.

The flange component 4 has a groove 4a to pinch the connecting collar 2c of the core component 2 and the connecting collar 6a of the tube component 6, ensuring the integration by connecting the core component 2 and the tube component 6 before pinched by the groove 4a.

After the integration, low temperature pyrolytic carbon is adhered to the region around the perimeter of the core component 2 and the flange component 4 by chemical vapor deposition (CVD) to integrate the core 2 and flange components 4.

Figure 2:
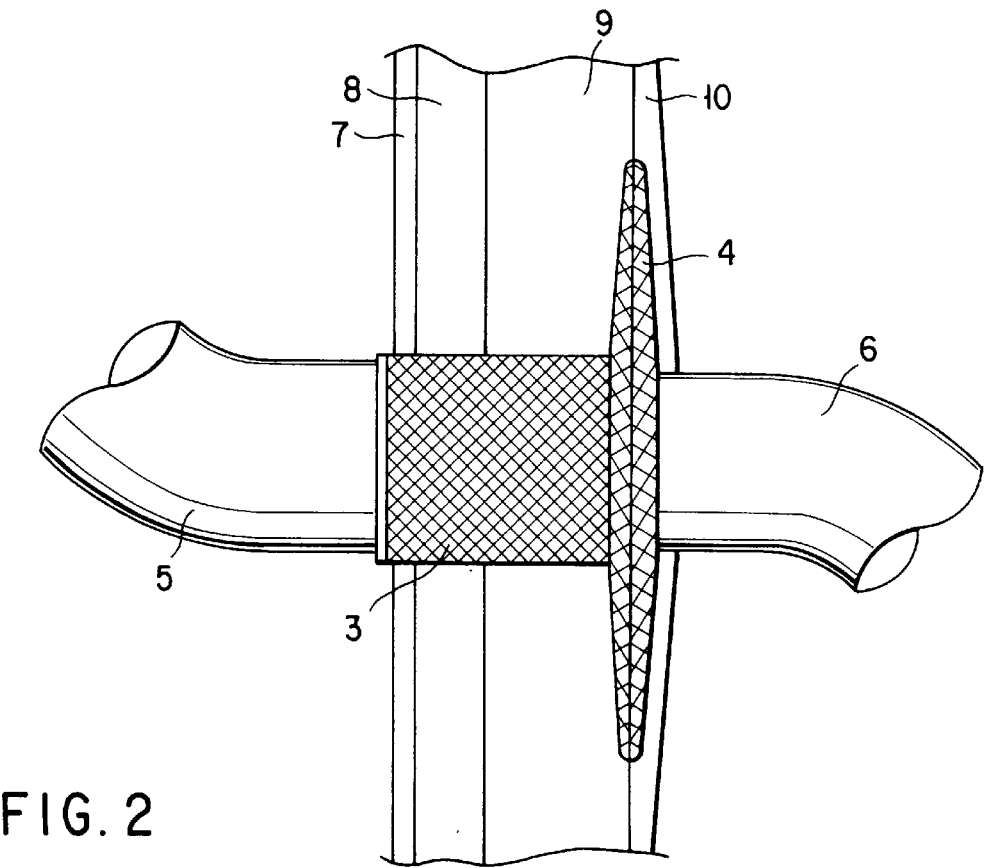
FIG. 2 is a longitudinal section view of the skin button of FIG. 1 buried in the subcutaneous tissue of the living body.

FIG. 2 is a expanded sectional view of the skin button in the present invention attached to the subcutaneous tissue. In this figure, the epidermis, dermis, straight muscle of abdomen and rectus sheath are designated by the numerals 7, 8, 9 and 10, respectively, and 7–10 as a whole are referred to the subcutaneous tissue.

The flange component 4 let the core component 2 with the inserted tube component 5 pass through the skin, then connects the connecting collar 2c of the core component 2 and the connecting collar 6a of the tube component 6 on the side of the artificial organ. The connected part is snapped in the groove 4a, and then buried between the straight muscle of abdomen 9 and the rectus sheath 10, ensuring the linkage of the tubes 5 and 6 from the artificial organ and the outer equipment, respectively, and the core component 2. The surface of the flange component 4 on which carbon fiber base materials treated with low temperature pyrolytic carbon by chemical vapor deposition like in the case around the perimeter of the core component 2, is well compatible with the subcutaneous tissue.

FIG. 3 is an explanatory drawing of the method to mount the fringe component 4 to the core component 2 in the present invention. In this figure, the numerals 2c, 6a and 30 are the connecting collar of the core component 2, the collar of the tube component 6 on the side of the artificial organ, and the screw component to connect flange component 4, respectively. After joining the connecting collar 6a of the tube component 6 on the side of the artificial organ to the connecting collar 2c of the core component 2 with tube component 5 on the side of the outer equipment attached, the junction is pinched by the groove 4a to attach the flange component 4 and secure it with the screw component 30 to link the core component 2 and the tube component 6. The method to secure is not limited to use of the screw component but include screw-in, caulking, bonding and the like. The above work establishes the linkage between the artificial organ and cables and the like from the outer equipment via the tube component 5, core component 2, and tube component 6, allowing various medical treatment (injection of drug solution, sampling of biological substances, etc.).

In the embodiment, the junction of the core component and the tube component on the side of the artificial organ is secured with the flange component, but the method is not limited to this and direct anchoring may be used.

Figure 4:
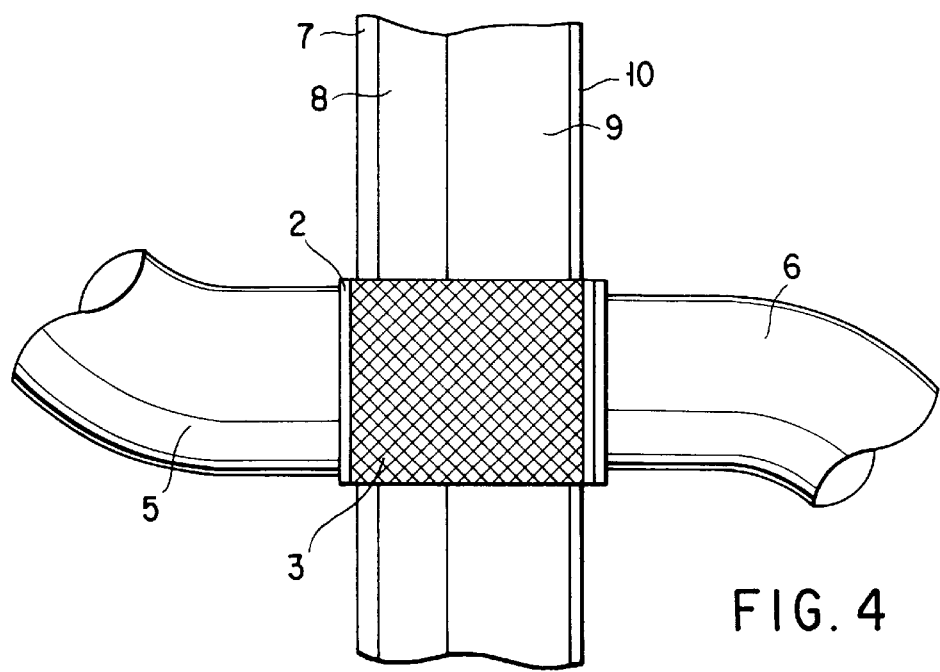
FIG. 4 is a side view of the skin button of FIG. 1 buried in the subcutaneous tissue without the flange component attached.

FIG. 4 is an expanded sectional view of a situation without flange component in the present invention.

It has the same configuration with that in FIG. 3 except that it has no flange component, and that the tubular component is secured to the subcutaneous tissue.

Since the muscle tissue in the skin has sufficient blood flow and has a marked resistance to infection, which makes it an effective protective barrier against transcutaneous infection, the core and flange components buried in the skin are unlikely to have any adverse effect on the living body, considering the fact that they also use carbon fiber base materials with favorable biocompatibility.

A surface layer of porous structure with a high percentage of void of carbon fiber base materials allows smooth and firm binding to the living body, and when the component is buried in the living body, the skin tissue invades into the pores of the porous structure layer, and the entangled carbon fibers and skin tissue enable a favorable bonding and fixing of the component to the skin tissue.

Moreover, since carbon fiber base materials are free of corrosion due to its carbonic surface, and have a good affinity with the living body, they stand up to a long-term use without causing any looseness after attached to the living body.

Figure 5:
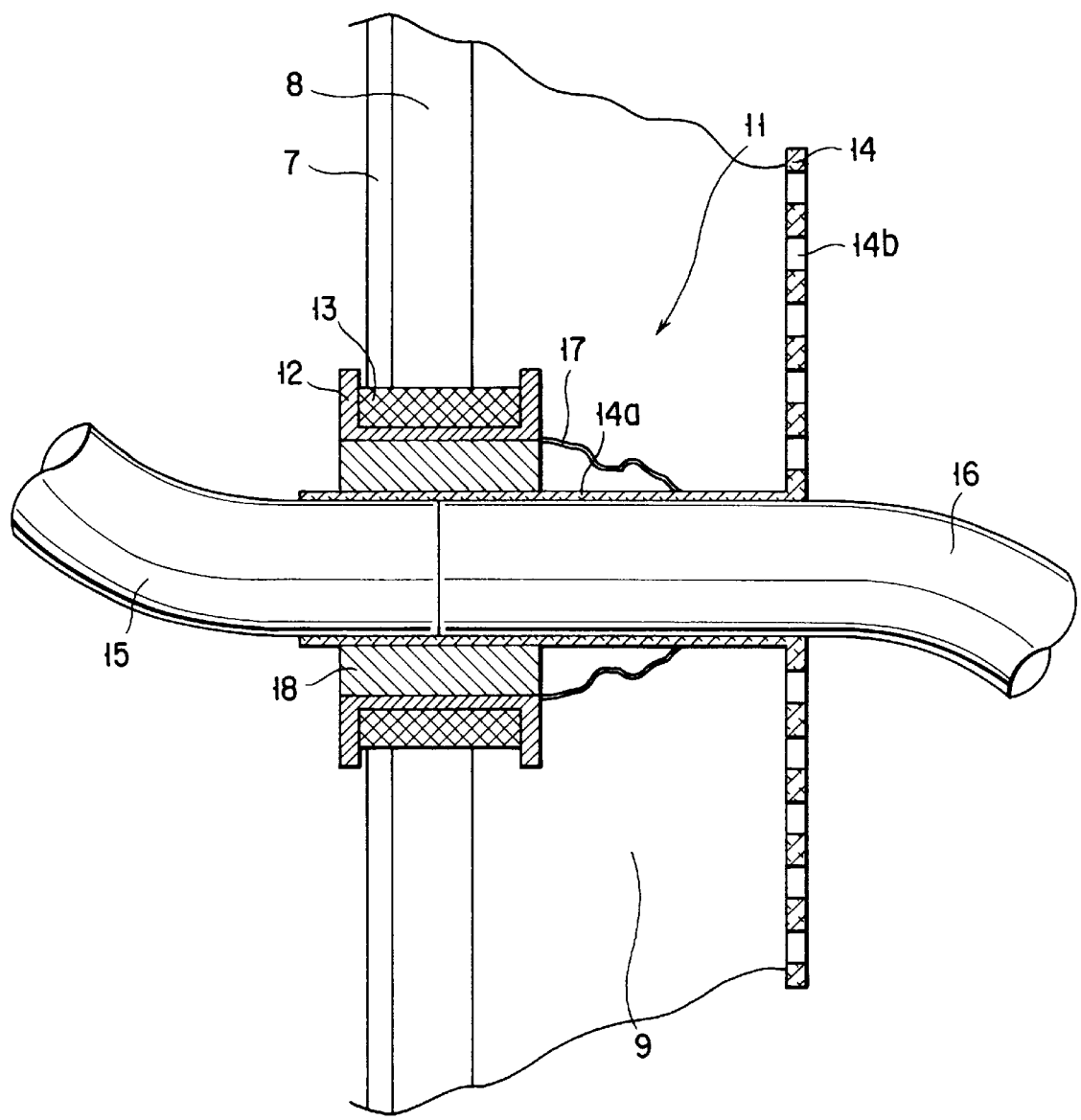
FIG. 5 is a longitudinal section view of the skin button in the embodiment 2 of the present invention.

FIG. 5 is an expanded sectional view illustrating the embodiment 2 of the skin button in the present invention.

In this figure, the numerals 7, 8, 9, 11, 12, 14, 17, and 18 are the epidermis, subcutaneous region, straight muscle of abdomen, skin button, core component, flange component, elastic membrane, and spacer, respectively.

The core component 12 is covered with the tubular component 13. The flange component is formed as an integrated part consisting of the tube component 15, the cylinder portion 14a holding the tube component 16, and the flat board containing multiple small holes 14b.

The flat board of the flange where small holes are prepared binds and securely adhered to the straight muscle of abdomen. The elastic membrane and spacer hold by the core and flange components allows relief of the relative slippage in the flange component movement due to the outer force transmitted to the penetrating site on the epidermis via the core component, reducing pain or stress imposing to the epidermis.

Figure 6:
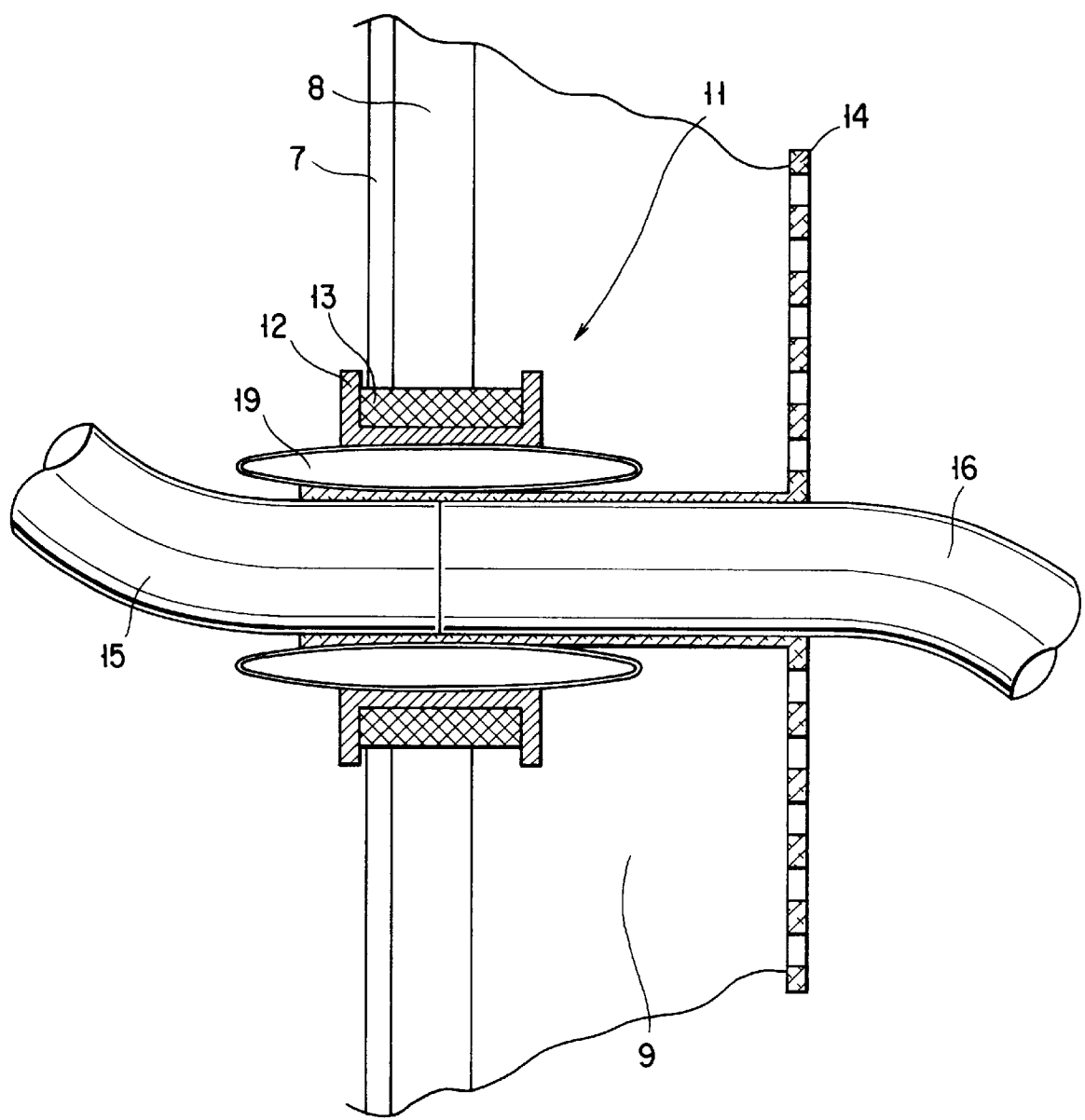
FIG. 6 is a longitudinal section view of the skin button in the embodiment 3 of the present invention.

FIG. 6 is an expanded sectional view of the embodiment 3 of the skin button in the present invention. In this embodiment, as shown in the figure, a hole membrane 19 is placed between the core component and the cylinder portion of the flange component, which allows the same action as the elastic membrane and spacer produces.

Figure 7:
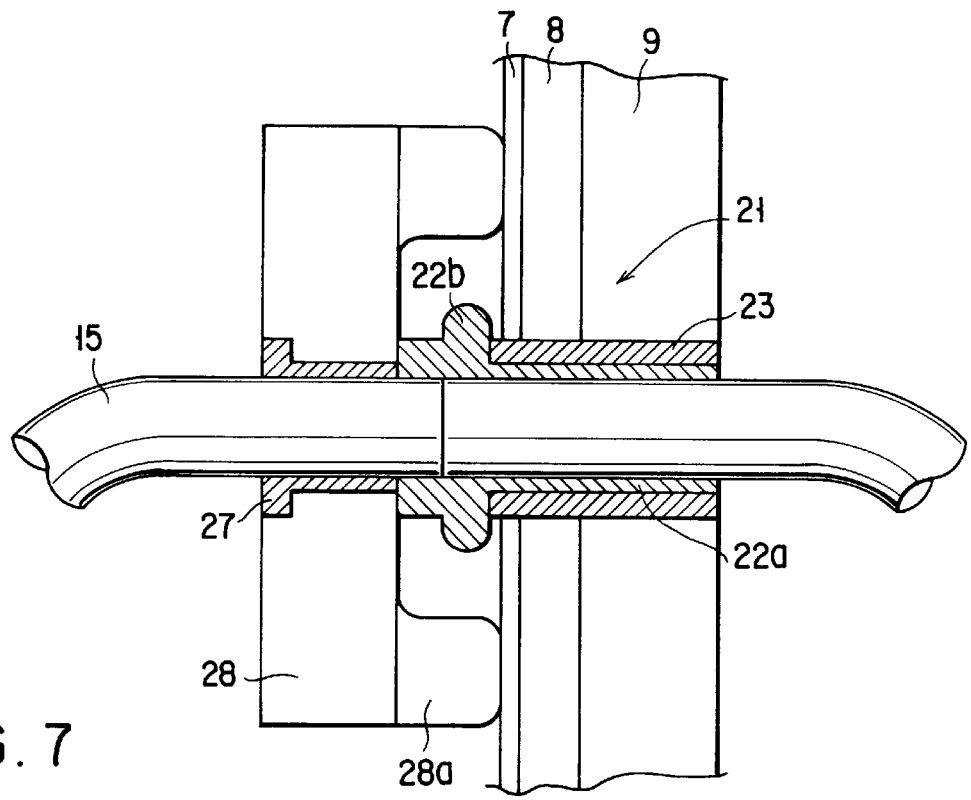
FIG. 7 is a longitudinal section view of the skin button in the embodiment 4 of the present invention.

FIG. 7 is an expanded sectional view of the embodiment 4 of the skin button in the present invention.

In the figure, the numerals 7, 8, 9, 21, 22, 23, 27 and 28 are the epidermis, subcutaneous region, straight muscle of abdomen, skin button, core component, tubular component, elastic component, and joint component, respectively.

In the core component 22, there are a through hole 22a in which the tube component 15 and the tube component 16 join, and the collar component 22b is attached on the side to the epidermis, and the flange component 24 to the other edge.

The core component 22 on the side of the collar component joins with the joint component 28 which hooks to the tube component 15 via the elastic component 27 and forms several protrusions 28a on the rim in a ring fashion.

These protrusions of the joint component can suppress the movement of the skin at the contact site and reduce a pain since the joint component hooks to the core component in a freely rotatable manner, and the protrusions change the contact position to a ring shape to press the region surrounding the epidermis where the core component passes through.

Moreover, they avoid inhibition of the bonding of the tubular component and the subcutaneous tissue.

In this embodiment, the core component and the fringe are integrated, but the fringe may be separately formed and hooked and attached to the core component.

Figure 8:
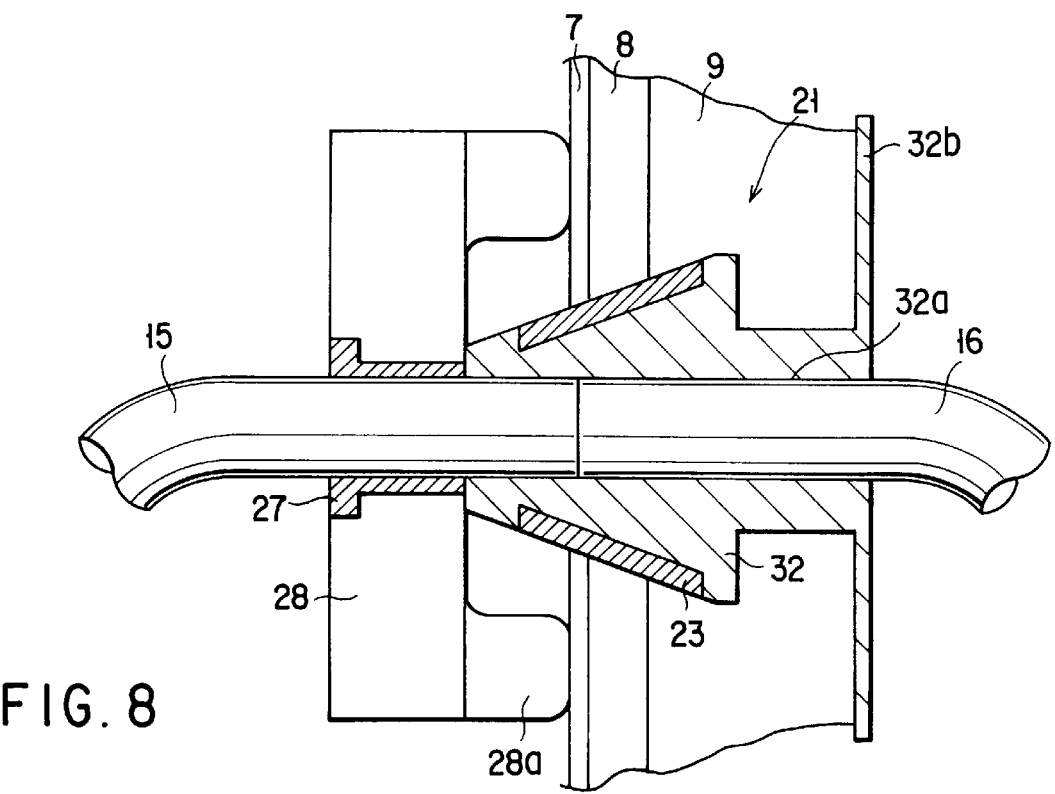
FIG. 8 is a longitudinal section view of the skin button in the embodiment 5 of the present invention.

FIG. 8 is an expanded sectional view of the embodiment 5 of the skin button in the present invention. Its configuration, as shown in the figure, is same as that of FIG. 7 except for the core component 32.

The core component 32 has a truncated corn on the side bonding to the epidermis and an integrated flange component 32b on the side bonding to the straight muscle of abdomen, as well as a through hole 32a in the center which holds the tube components 15 and 16, and the tubular component 23 covering the trapezoidal bevel of the core component.

The covering of the trapezoidal bevel with the tubular component 23 allow the prevention of down growth, that is, an abnormal skin growth at the skin contact site. The protrusions of the joint component can suppress the movement of the skin at the contact site and reduce a pain since the joint component hooks to the core component in a freely rotatable manner, and the protrusions change the contact position to a ring shape to press the region surrounding the epidermis where the core component passes through.

Moreover, they avoid inhibition of the bonding of the tubular component and the subcutaneous tissue.

In the embodiment, the core component and the fringe are integrated, but the fringe may be separately formed and hooked and attached to the core component.

Figure 9:
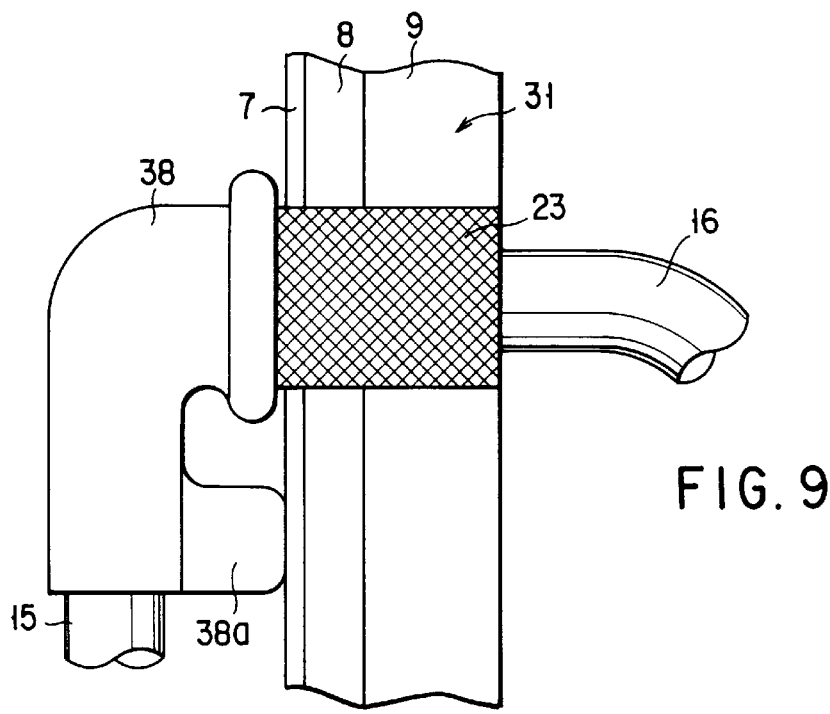
FIG. 9 is a side view of the skin button in the embodiment 6 of the present invention.

FIG. 9 is an expanded sectional view of the embodiment 6 of the skin button in the present invention. In the figure, the numerals 7, 8, 9, 31, 33, 34 and 38 are the epidermis, subcutaneous region, straight muscle of abdomen, skin button, tubular component attached to the rim of the core component, flange component hooked to the core component, and the joint component, respectively.

One end of the joint component 38 is made in a bending form to be in parallel with the epidermis and hooked to the core component on the side to the epidermis, while the other end is hooked to the tube component 15 with multiple protrusions 38a formed in a ring fashion on the rim in order to push the epidermis. These protrusions 38a of the joint component press the epidermis around the site where the core component passes, inhibiting the movement of the skin and reducing pain, as well as preventing bacterial infection similar to the case in FIG. 7.

Figure 10:
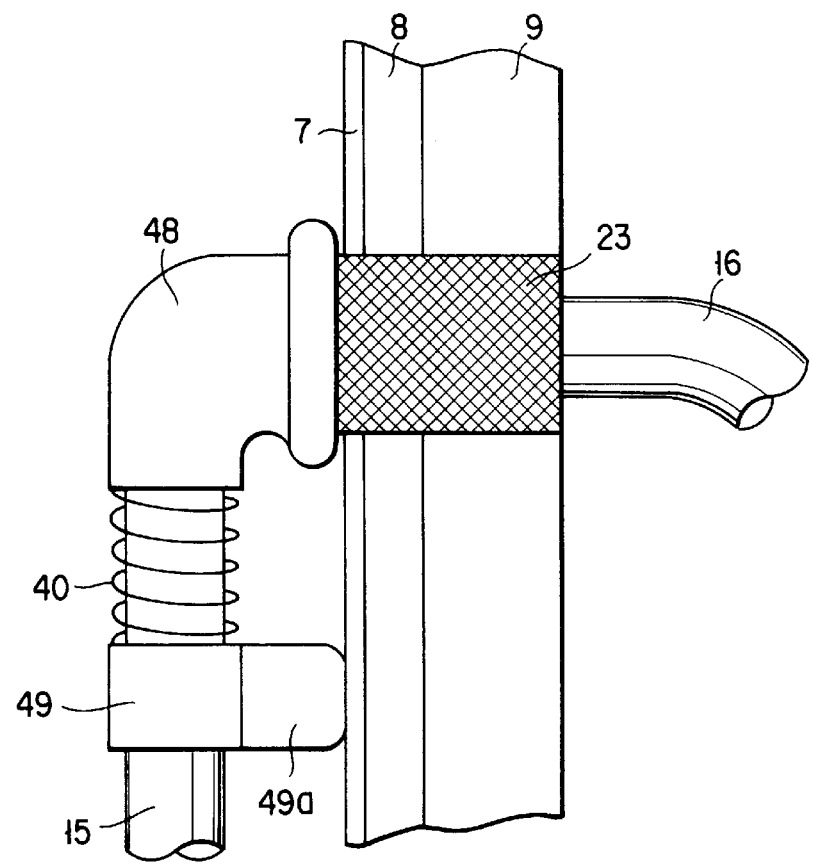
FIG. 10 is a side view of the skin button in the embodiment 7 of the present invention.

FIG. 10 is an expanded sectional view of the embodiment 7 of the skin button in the present invention.

In the figure, its configuration is similar to that of FIG. 9 except for the joint component 48 and the protrusion component 49.

The joint component 48 is made in such a bending form to be in parallel with the epidermis and hooked to the core component on the side to the epidermis, while the other end is hooked to the tube component 15 with the protrusion component 49 where multiple protrusions 49a formed in a ring fashion on the rim in order to push the epidermis. Between the joint component 48 and the protrusion component 49, the elastic component 40 hooking to the tube component 15 is attached.

The elastic component 40 allows relief of the stimulation to the skin by the movement of the tube component 15, and also inhibits the movement of the skin and reduces pain as well as prevents bacterial infection in cooperation with the protrusions 49a which are pressure components pressing the epidermis around the site where the core component passes.

Figure 11:
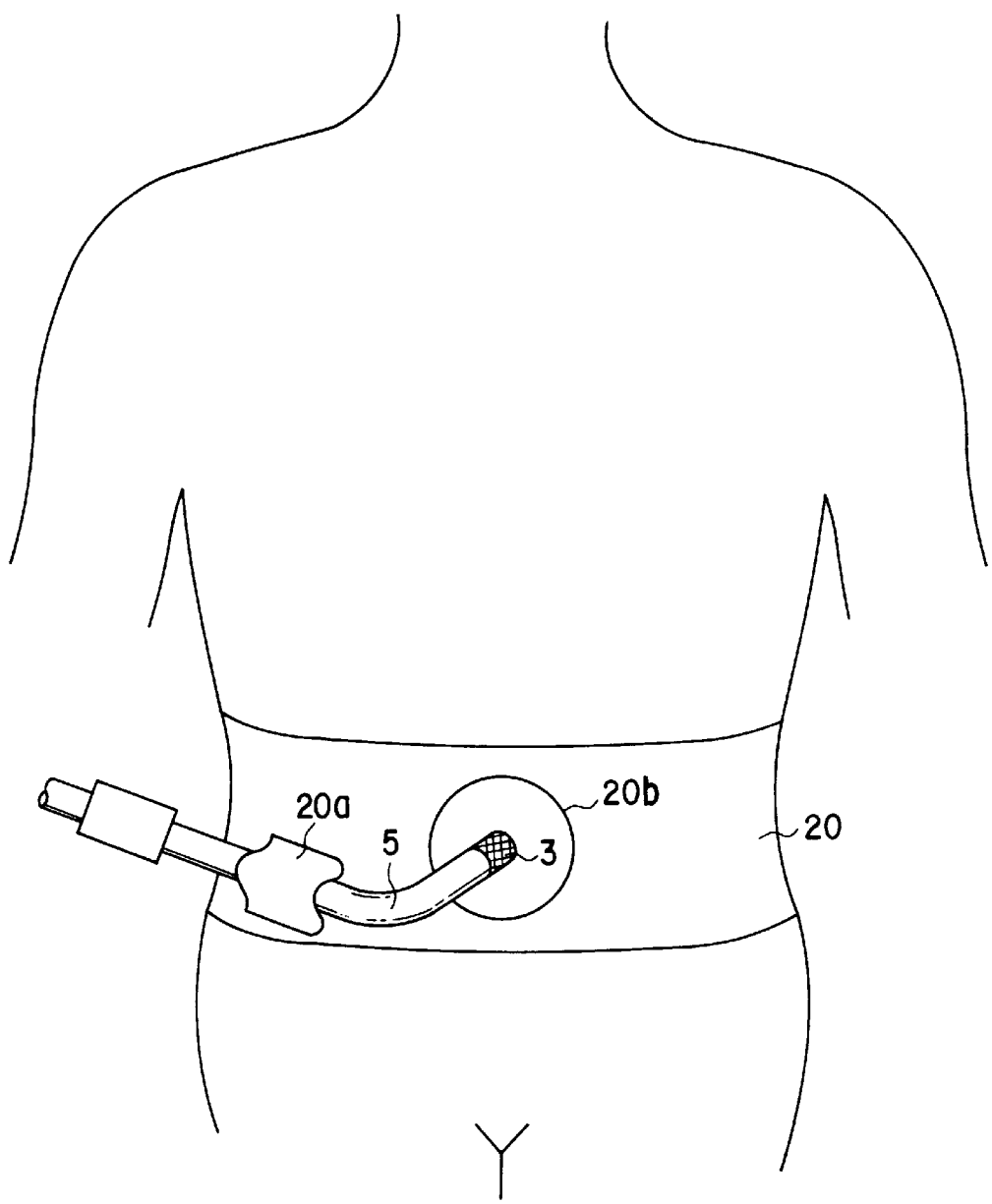
FIG. 11 is a front view of the skin button in the embodiment 8 of the present invention attached to the living body.

FIG. 11 is an explanatory drawing where the belt is worn around the human body.

In the figure, the numerals 3, 5 and 20 are the tubular component secured to the rim of the core component, the tube component on the side of the outer equipment which is hooked to the core component, and the belt, respectively.

The belt 20 has a holder 20a which sustains the tube component 5 secured to the surface of the belt 20, and a through hole 20b whose diameter is larger than the outer diameter of the tube component 5. Since the tube component 5 is sustained by the holder 20a, the movement of the tube component would not be directly transmitted to the core component, relieving pain in the epidermis. Moreover, since the rim of the core component attached is pressed by the through hole 20b formed in the belt, the movement of the epidermis is minimized, reducing pain in the epidermis.

Since the muscle tissue in the skin has sufficient blood flow and has a marked resistance to infection, which makes it an effective protective barrier against transcutaneous infection, the core and flange components buried in the skin are unlikely to have any adverse effect on the living body, considering the fact that they also use carbon fiber base materials with favorable biocompatibility. A surface layer of porous structure with a high percentage of void of carbon fiber base materials allows smooth and firm bind the skin to tissue of the living body, and when the component is buried in the living body, the skin tissue invades into the pores of the porous structure layer, and the entangled carbon fibers and skin tissue enable a favorable bonding and fixing of the component to the skin tissue.

Moreover, since carbon fiber base materials are free of corrosion due to its carbonic surface, and have a good affinity with the living body, they stand up to a long-term use without causing any looseness after attached to the living body.

The embodiment describes the skin button connected to the artificial heart, but not limited to it, and similar effects can be obtained in the skin buttons used in connection of not only an artificial organ but also a living organ with an outer equipment, injection of drug solution, sampling of biological substances, input/output of electric signals, skin penetrating transcutaneous attachment for a long term indwelling.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A skin button secured in the subcutaneous tissue of a living body, which lets pass through skin penetrating components connecting a living organ or an artificial organ in the body to equipment outside the body, said skin button comprising:

a cylindrical core component having at least one through hole through which said skin penetrating components pass; and a tubular component composed of biocompatible fibrous materials attached at least to part of an outer circumference of the core component in contact with living tissue, wherein chemical vapor deposited low-temperature pyrolytic carbon is adhered at least to said part of the tubular component in contact with the living body.

2. The skin button according to claim 1 wherein a flange protrudes from the outer circumference of one end of said core component, and said low-temperature chemical vapor deposited pyrolytic carbon is adhered at least to said flange which contacts the living body.

3. The skin button according to claim 2, wherein said flange is attachable to, and detachable from said core component.

4. The skin button according to claim 1, wherein said low-temperature pyrolytic carbon coating on said tubular component and said flange is treated with oxide plasma.

5. The skin button according to claim 1, wherein said skin penetrating components are housed in coated tubes, and end portions of said coated tubes are attached to respective ends of said core component.

6. The skin button according to claim 1, further comprising a belt for wearing and retaining the skin button on the human body, said belt comprising a holder portion for holding said tube on a side of equipment outside the body, and a through hole having a diameter larger than the outer diameter of said tube, said belt supporting the outer circumference of said skin button outside the living body by pressing and holding the skin button thereagainst with belt portions surrounding said through hole.

\* \* \* \* \*

UNITED STATES PATENT AND TRADEMARK OFFICE
CERTIFICATE OF CORRECTION

PATENT NO. : 5,971,962
DATED     : October 26, 1999
INVENTOR(S) : KOJIMA et al

It is certified that error appears in the above-identified patent and that said Letters Patent is hereby corrected as shown below:

On the Title Page Item [73] Assignee should read as follows --Sun Medical Technology Research Corporation, Nagano, Japan--.

Signed and Sealed this

Twenty-sixth Day of September, 2000

Attest:

Q. TODD DICKINSON

*Attesting Officer*        *Director of Patents and Trademarks*